United States Patent
Maerz et al.

(10) Patent No.: US 10,899,683 B2
(45) Date of Patent: Jan. 26, 2021

(54) PROCESS FOR PRODUCING ETHYLBENZENE

(71) Applicant: BADGER LICENSING LLC, Boston, MA (US)

(72) Inventors: Brian Maerz, Chelmsford, MA (US); Chung-Ming Chi, Needham, MA (US); Raghavender Bhoomi, South Weymouth, MA (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 16/070,585

(22) PCT Filed: Feb. 17, 2016

(86) PCT No.: PCT/US2016/018245
§ 371 (c)(1),
(2) Date: Jul. 17, 2018

(87) PCT Pub. No.: WO2017/142526
PCT Pub. Date: Aug. 24, 2017

(65) Prior Publication Data
US 2019/0016647 A1   Jan. 17, 2019

(51) Int. Cl.
C07C 2/66 (2006.01)
C07C 6/12 (2006.01)
B01J 29/03 (2006.01)
B01J 29/06 (2006.01)
B01J 29/08 (2006.01)
B01J 29/18 (2006.01)
B01J 29/70 (2006.01)

(52) U.S. Cl.
CPC ............. *C07C 2/66* (2013.01); *B01J 29/0308* (2013.01); *B01J 29/06* (2013.01); *B01J 29/08* (2013.01); *B01J 29/18* (2013.01); *B01J 29/7007* (2013.01); *C07C 6/126* (2013.01); *C07C 2529/06* (2013.01); *C07C 2529/08* (2013.01); *C07C 2529/18* (2013.01); *C07C 2529/70* (2013.01); *Y02P 20/52* (2015.11)

(58) Field of Classification Search
CPC ....... C07C 2/66; C07C 6/126; C07C 2529/06; C07C 2529/08; C07C 2529/18; C07C 2529/70; B01J 29/06; B01J 29/08; B01J 29/18; B01J 29/7007; B01J 29/0308; Y02P 20/52
See application file for complete search history.

(56) References Cited

U.S. PATENT DOCUMENTS

| | | | | |
|---|---|---|---|---|
| 5,856,607 A | * | 1/1999 | Kim | C07C 15/073 585/314 |
| 7,622,622 B1 | * | 11/2009 | Woodle | C07C 2/66 585/467 |
| 2007/0161835 A1 | * | 7/2007 | Butler | B01J 29/7057 585/446 |
| 2007/0265481 A1 | * | 11/2007 | Clark | C07C 2/66 585/449 |
| 2008/0058566 A1 | * | 3/2008 | Butler | B01J 29/06 585/448 |
| 2008/0289946 A1 | * | 11/2008 | Schultz | B01D 3/14 202/153 |

FOREIGN PATENT DOCUMENTS

WO   94/13603 A1   6/1994
WO   2006107470 A1   10/2006

OTHER PUBLICATIONS

International Search Report and Written Opinion issued in a corresponding application PCT/US2016/018245 dated Oct. 20, 2016.

* cited by examiner

*Primary Examiner* — Youngsul Jeong
*Assistant Examiner* — Jason Y Chong
(74) *Attorney, Agent, or Firm* — Roberts Calderon Safran & Cole P.C.

(57) ABSTRACT

A process for producing ethylbenzene is described in which benzene and ethylene are supplied to an alkylation reaction zone. Also added to the alkylation reaction zone is a $C_{3+}$ olefin in an amount of at least 200 ppm by weight of the ethylene supplied to the alkylation reaction zone. The benzene, ethylene and $C_{3+}$ olefin are contacted with an alkylation catalyst in the alkylation reaction zone to alkylate at least part of the benzene and produce an alkylation effluent comprising ethylbenzene, polyethylated benzene and at least one mono-$C_{3+}$ alkyl benzene. The alkylation effluent is separated into a first product fraction comprising ethylbenzene and a second fraction comprising polyethylated benzene and the at least one mono-$C_{3+}$ alkyl benzene. The second fraction is then contacted with benzene in the presence of a transalkylation catalyst to convert at least part of the polyethylated benzene to ethylbenzene and produce a transalkylation effluent.

12 Claims, No Drawings

PROCESS FOR PRODUCING ETHYLBENZENE

CROSS-REFERENCE TO RELATED APPLICATIONS

The present application is a U.S. National Phase of PCT/US2016/018245 filed on Feb. 17, 2016. The disclosure of the PCT Application is hereby incorporated by reference into the present Application.

FIELD

This invention relates to a process for producing ethylbenzene.

BACKGROUND

Ethylbenzene is a valuable commodity chemical which is used industrially for the production of styrene monomer, most of which is used to make polystyrene. Ethylbenzene is produced commercially by a chemical process which includes two reaction steps, both generally conducted over zeolite catalysts. In the first reaction step, benzene is alkylated with ethylene, with the benzene being in excess, to form ethylbenzene and smaller amounts of di- and triethylbenzenes (referred to collectively as polyethylated benzenes or PEB). Unreacted benzene, ethylbenzene product and polyethylated benzenes are recovered in a distillation system as separate streams. In a second reaction step, the recovered polyethylated benzenes are converted to additional ethylbenzene by transalkylation with benzene. The overall reaction also generates some heavy ($C_{13+}$) aromatic hydrocarbons, generally referred to as EB residue, which can be used as a heat transfer fluid, a transformer oil and/or an absorber oil for the recovery of lighter aromatics from vent gas streams.

Although the above process is widely and successfully practiced on a commercial scale, there is a continuing need to increase the production capacity of EB plants without increasing capital costs. This is a particular issue in the transalkylation stage of many plants where the capacity is often limited by the quantity of the transalkylation catalyst.

According to the present invention, it has now been found that the presence of $C_{3+}$ alkylbenzenes, particularly propylbenzenes and butylbenzenes, in the feed to the transalkylation stage of the ethylbenzene production process promotes the conversion of polyethylated benzenes in the feed. As a result, the amount of PEB recycle can be reduced thereby debottlenecking the PEB recovery and transalkylation systems of the plant. Typically, the amount of $C_{3+}$ alkylbenzenes produced in the alkylation stage of an EB plant is quite small (normally less than 1000 ppm by weight), especially using polymer grade ethylene as the alkylating agent. However, the amount of $C_{3+}$ alkylbenzenes produced in the alkylation stage can be increased by the deliberate addition of $C_{3+}$ olefins, particularly propylene and/or butenes, to the alkylation feed. Moreover, it is found that the $C_{3+}$ alkylbenzenes react with other alkylbenzenes during the transalkylation process to produce diarylalkanes, which can add value to the EB residue stream.

SUMMARY

Thus, in one aspect, the invention resides in a process for producing ethylbenzene, the process comprising:

(a1) supplying benzene and an alkylating agent comprising at least 40 wt % ethylene to an alkylation reaction zone;

(b1) adding at least one $C_{3+}$ olefin to the alkylation reaction zone in an amount of at least 200 ppm by weight of the ethylene supplied to the alkylation reaction zone; and (c1) contacting the benzene, ethylene and $C_{3+}$ olefin with an alkylation catalyst in the alkylation reaction zone under alkylation conditions effective to alkylate at least part of the benzene and produce an alkylation effluent comprising ethylbenzene, polyethylated benzene and at least one mono-$C_{3+}$ alkyl benzene;

(d1) separating the alkylation effluent into at least a first product fraction comprising ethylbenzene and a second fraction comprising polyethylated benzene and said at least one mono-$C_{3+}$ alkyl benzene; and (e1) contacting at least part of the second fraction with benzene in the presence of a transalkylation catalyst under transalkylation conditions effective to convert at least part of the polyethylated benzene to ethylbenzene and produce a transalkylation effluent.

DETAILED DESCRIPTION

As used herein, the term "$C_n$" hydrocarbon wherein n is a positive integer, e.g., 1, 2, 3, 4, 5, means a hydrocarbon having n number of carbon atom(s) per molecule. The term "$C_{n+}$" hydrocarbon wherein n is a positive integer, e.g., 1, 2, 3, 4, 5, as used herein, means a hydrocarbon having at least n number of carbon atom(s) per molecule. The term "$C_{n-}$" hydrocarbon wherein n is a positive integer, e.g., 1, 2, 3, 4, 5, as used herein, means a hydrocarbon having no more than n number of carbon atom(s) per molecule.

As used herein, the term "mono-$C_{3+}$ alkyl benzene" means a monalkylated benzene having one alkyl group with at least 3 carbons atoms. In some embodiments, the mono-$C_{3+}$ alkyl benzene comprises a propylbenzene, such as n-propylbenzene and/or cumene, and/or a butylbenzene, such as n-butylbenzene, sec-butylbenzene and/or t-butylbenzene.

Described herein is a process for producing ethylbenzene in which benzene is alkylated with ethylene to form ethylbenzene and smaller amounts of di- and triethylbenzenes (referred to collectively as polyethylated benzenes or PEB) and, after recovery of at least part of the ethylbenzene, the polyethylated benzenes are transalkylated with additional benzene to produce further ethylbenzene. In the present process, the conversion of polyethylated benzenes in the transalkylation step is promoted by the addition to the transalkylation feed of at least one mono-$C_{3+}$ alkyl benzene. The mono-$C_{3+}$ alkyl benzene additive is conveniently produced by the addition of at least one $C_{3+}$ olefin, particularly propylene and/or butene, to the alkylation step.

Alkylation

Any commercially available benzene feed can be used in the alkylation step of the present process, but in most embodiments the benzene is arranged to have a purity of at least 99.5 wt %, such as at least 99.8 wt %. In some embodiments, the benzene may be treated prior to being introduced to the alkylation reaction, for example to reduce the level of water to less than 20 ppm by weight and/or the level of organic nitrogen compounds to less than 0.03 ppm by weight as N.

The main alkylating agent employed in the present process comprises ethylene, which can be present as a substantially pure feed, namely with a purity of at least 99.9 mol %, such as at least 99.95 mol %, or as a mixture with one or more non-reactive diluents, such as alkanes, especially ethane. In some embodiments, the ethylene (sometimes referred to herein as the ethylene-containing feed) is introduced to the alkylation reaction as a mixture and may contain at least 40 wt %, for example at least 50 wt %, such as at least 80 wt %, for example at least 90 wt %, such as at least 95%, ethylene. In some embodiments, the ethylene-containing feed may be treated prior to being introduced to the alkylation reaction, for example to reduce the level of organic nitrogen compounds to less than 0.03 ppm by weight as N.

In some embodiments, at least one $C_{3+}$ olefin, such as propylene and/or one or more butenes, is deliberately added into the alkylation reaction zone in addition to the ethylene-containing feed. By "deliberately added", it is meant that the $C_{3+}$ olefin is added to the alkylation reaction zone in amounts in excess of any $C_{3+}$ olefins that may be present in the ethylene-containing feed as impurities. The $C_{3+}$ olefin can be introduced into the alkylation reaction zone separately from the ethylene-containing feed or can be mixed with the ethylene-containing feed prior to introduction of the mixture. Generally, the $C_{3+}$ olefin is added to the alkylation reaction zone in an amount comprising at least 200 ppm, such as at least 500 ppm, for example at least 1,000 ppm, such as at least 2,500 ppm, for example at least 5000 ppm, by weight of the ethylene fed to the alkylation reaction zone. In some embodiments, the $C_{3+}$ olefin is added to the alkylation reaction zone in an amount up to 20,000 ppm, for example up to 15,000 ppm, by weight of the ethylene fed to the alkylation reaction zone. In terms of ranges, the $C_{3+}$ olefin weight percent (wt %) relative to the ethylene fed to the alkylation reaction zone, may be from 0.02 to 2 wt %, such as from 0.05 to 1.1 wt %, for example from 0.1 to 1 wt %, such as 0.1 to 0.5 wt. %.

The alkylation reaction is conducted in the presence of at least one alkylation catalyst. Although any known alkylation catalyst can be employed in the present process, in most embodiments a heterogeneous solid acid catalyst, such as a molecular sieve, is preferred.

In one embodiment, the alkylation catalyst employed in the present process comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016, 245. ZSM-48 is more particularly described in U.S. Pat. No. 4,234,231.

In another embodiment, the alkylation catalyst employed in the present process comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250, 277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513) and mixtures thereof.

In a further embodiment, the alkylation catalyst employed in the present process comprises one or more large pore molecular sieves having a Constraint Index less than 2. Suitable large pore molecular sieves include zeolite beta, zeolite Y, Ultrastable Y (USY), Ultrahydrophobic Y (UHP-Y), Dealuminized Y (Deal Y), mordenite, ZSM-3, ZSM-4, ZSM-14, ZSM-18, ZSM-20 and mixtures thereof. Zeolite ZSM-3 is described in U.S. Pat. No. 3,415,736. Zeolite ZSM-4 is described in U.S. Pat. No. 4,021,947. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766, 093 and 3,894,104.

Preferred molecular sieves for the alkylation reaction comprise zeolite beta, molecular sieves having a Constraint Index of 2-12, especially ZSM-5, and molecular sieves of the MCM-22 family.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation reaction can be conducted in any suitable reactor such as a fixed bed reactor, a moving bed reactor, a fluidized bed reactor and a reaction distillation unit. A fixed bed reactor is generally preferred. In addition, although a single alkylation reactor can be employed, in some embodiments multiple reactors connected in series can be used with each reactor containing one or more of the catalysts described above.

The conditions in the alkylation reactor are selected so that some, and preferably all, of the ethylene in the olefin feed reacts with the benzene to form ethylbenzene together with some polyethylated benzenes. In addition, where present in the alkylation feed, some, and preferably all, of the $C_{3+}$ olefin in the olefin feed reacts with the benzene to form at least one mono-$C_{3+}$ alkyl benzene. Suitable conditions for the alkylation reaction include a temperature from 120° C. to 270° C., a pressure from 500 kPa-a to 8,300 kPa-a and a molar ratio of benzene to alkylating agent from 100:1 to 0.3:1. In some embodiments, the alkylation conditions include a temperature from 170° C. to 285° C., a pressure from 2000 kPa-a to 6000 kPa-a and a molar ratio of benzene to alkylating agent from 1.2:1 to 6:1. Where a fixed bed reactor is used, the alkylation conditions are selected such that at least part of the benzene (such as at least 50 wt % of the benzene) is in the liquid phase.

Alkylation Effluent Separation

In addition to the desired ethylbenzene, the effluent from the alkylation reaction normally contains significant quantities of unreacted benzene, together with smaller quantities of polyethylated benzenes. Moreover, in some embodiments, where at least one $C_{3+}$ olefin is added to the alkylation feed, the alkylation reaction effluent may contain one or more mono-$C_{3+}$ alkyl benzenes, especially propylbenzenes and/or butylbenzenes. Thus, the alkylation effluent is passed to a product separation system, such as a distillation train, that not only serves to recover the unreacted benzene and the desired ethylbenzene, but also separates a heavy fraction containing at least part of the polyethylated benzenes and any mono-$C_{3+}$ alkyl benzene. The unreacted benzene is recycled to the alkylation section and/or the transalkylation section, while the heavy fraction is fed to the transalkylation section, as described below.

Fresh benzene can be fed to the alkylation section, the transalkylation section or to the product separation section. In some embodiments, the fresh benzene feedstock is supplied to the product separation system to reduce the water content of the feedstock to less than 20 ppm by weight, such as less than 10 ppm by weight.

Transalkylation

In the transalkylation step of the present process, the heavy fraction from the product separation system is fed to a transalkylation reactor, where it is contacted with benzene in the presence of a transalkylation catalyst and under transalkylation conditions effective to convert at least part of the polyethylated benzene in the heavy fraction to ethylbenzene. Typically, the heavy fraction contains at least 20 wt %, for example at least 85 wt %, such at least 98 wt %, for example at least 99 wt %, polyethylated benzenes and less than 2 wt %, such as less than 1 wt %, benzene and ethylbenzene combined.

Also present in the transalkylation feed is at least one mono-$C_{3+}$ alkyl benzene, preferably a propylbenzene and/or a butylbenzene, either produced by deliberate addition of $C_{3+}$ olefin to the alkylation reaction zone or deliberately supplied to the transalkylation reactor from a separate source. Generally, the total feed to the transalkylation reactor comprises at least 1,000 ppm by weight, such as at least 2,000 ppm by weight, for example at least 3,000 ppm by weight of added mono-$C_{3+}$ alkyl benzene. In some embodiments, the feed to the transalkylation reactor comprises up to 20,000 ppm by weight, such as up to 18,000 ppm by weight, for example up to 15,000 ppm by weight of added mono-$C_{3+}$ alkyl benzene. In terms of ranges the feed to the transalkylation reactor may comprise from 1,000 to 18,000 ppm by weight, for example from 3,000 to 15,000 ppm by weight of added mono-$C_{3+}$ alkyl benzene. It is to be appreciated that the transalkylation feed may inherently contain a non-zero base level of mono-$C_{3+}$ alkyl benzene resulting from impurities in the ethylene-containing alkylation feedstock. For clarity, the references herein to added mono-$C_{3+}$ alkyl benzene are directed to levels of mono-$C_{3+}$ alkyl benzene independent of this base level. Thus, as will be demonstrated in the following Example, the addition of such mono-$C_{3+}$ alkyl benzene to the transalkylation feed is found to promote the conversion of the polyethylated benzenes in the heavy fraction to ethylbenzene.

The total feed to the transalkylation reactor typically contains 33 wt % to 94 wt % benzene.

The transalkylation catalyst can comprise one or more of any of the molecular sieves discussed above in relation to the alkylation system and can be used with or without a binder or matrix. Generally, however, the transalkylation catalyst is selected from zeolite beta, zeolite Y, Ultrastable Y (USY), Dealuminized Y (Deal Y), mordenite, ZSM-3, ZSM-4, ZSM-5, ZSM-11, ZSM-18, ZSM-20, MCM-22, PSH-3, SSZ-25, ERB-1, ITQ-1, ITQ-2, MCM-36, MCM-49, MCM-56, UZM-8, UZM-8HS and mixtures thereof. Preferred transalkylation catalysts comprises at least one zeolite selected from zeolite beta, zeolite Y, mordenite and a molecular sieve of the MCM-22 family.

Suitable conditions for carrying out the transalkylation step include a temperature of from about 100° C. to about 300° C., a pressure of 8,000 kPa-a or less, a WHSV based on the weight of the total liquid feed to the reaction zone of from about 0.5 to about 100 hr' and a mole ratio of benzene to polyethylated benzene of from about 1:1 to about 30:1. In some embodiments, the transalkylation conditions are selected such that the reactants are at least partially or predominantly (greater than 50 wt %) in the liquid phase.

The transalkylation reaction is normally carried out in a separate reaction zone from that employed to effect the alkylation step.

Transalkylation Effluent Separation

The effluent from the transalkylation reaction contains ethylbenzene, normally together with unreacted benzene and some heavy ($C_{13+}$) by-products. The effluent is passed to a product separation system for recovery of the unreacted aromatic compound and the desired ethylbenzene. The separation system can also include provision for recovery of the heavy ($C_{13}+$) by-products, which typically include valuable diarylalkanes. In some embodiments, the same product separation system is used to separate the alkylation effluent and the transalkylation effluent.

Alternative embodiments of the invention comprise:

A. A process for producing ethylbenzene, the process comprising:

(a2) providing a transalkylation feed comprising at least 20 wt % polyethylated benzene;

(b2) adding at least one mono-$C_{3+}$ alkyl benzene to the transalkylation feed in an amount of at least 1,000 ppm by weight; and then (c2) contacting the transalkylation feed with benzene in the presence of a transalkylation catalyst under transalkylation conditions effective to convert at least part of the polyethylated benzene to ethylbenzene and produce a transalkylation effluent.

B. A process according to embodiment A, wherein the mono-$C_{3+}$ alkyl benzene comprises a propylbenzene and/or butylbenzene.

C. A process according to embodiments A or B, wherein the amount of mono-$C_{3+}$ alkyl benzene is added to the transalkylation feed in an amount of from 1,000 ppm to 20,000 ppm by weight.

D. A process according to any one of embodiments A to C, wherein the transalkylation catalyst comprises at least one zeolite selected from zeolite beta, zeolite Y, mordenite and a molecular sieve of the MCM-22 family.

E. A process according to any one of embodiments A to D, wherein the transalkylation conditions include a temperature from 100° C. to 300° C., a pressure of 8,000 kPa or less, a WHSV from 0.5 to 100 hr$^{-1}$ and a mole ratio of benzene to polyethylated benzene of from about 1:1 to about 30:1.

F. A process according to any one of embodiments A to E, wherein the transalkylation conditions are selected such that the transalkylation feed is at least partially in the liquid phase.

G. A process according to any one of embodiments A to F and further comprising:

(d2) separating a product fraction comprising ethylbenzene from the transalkylation effluent.

H. A process according to any one of embodiments A to G and further comprising:

(e2) separating a $C_{13+}$ aromatic hydrocarbon fraction comprising diarylalkanes from the transalkylation effluent.

The invention will now be more particularly described in the following non-limiting Example.

EXAMPLE

Table 1 shows the results of adding propylbenzene and/or butylbenzene to the feed to the transalkylation section of a pilot plant for producing ethylbenzene.

The pilot plant included an alkylation section having multiple series-connected fixed bed alkylation reactors each containing a zeolite catalyst and a transalkylaton section having a single fixed bed transalkylation reactor containing a zeolite catalyst.

As shown in the Table, the conditions in the transalkylation section included an average temperature of 205° C., an outlet pressure of 400 psig (2859 kPa-a), a benzene to polyethylated benzene molar ratio of 2 and a WHSV on total feed of 3.3 hr$^{-1}$.

The Table details the change in % conversion of total PEBs in the transalkylation feed as the amount of propylbenzene and/or butylbenzene added to the feed was varied.

The data reported start with "Feed-B1" on stream as the base case situation. At this time and for the next 69 hours, the transalkylation feed was reacted with no propylbenzene and/or butylbenzene being deliberately added to the feed. The Feed-B1 was a composite feed from a pilot plant used to conduct a variety of alkylation reactions and was found to contain 3038 ppm of propylbenzene and butylbenzene combined (higher than would be found in a commercial ethylbenzene plant). The average PEB conversion during the first 69 hours was 59.4%.

After 69 hours on stream, a mixture of propylbenzene and butylbenzene was added to the feed to achieve an increase of 905 ppm by weight of propylbenzene (PB) and 232 ppm by weight of butylbenzene (BB) relative to base case Feed-B1. After a further 19 hours (Column "Effluent-D1S1") the PEB conversion was again measured and had increased by over 4% to 63.7%.

After 118 hours on stream, a mixture of propylbenzene and butylbenzene was added to the feed to achieve an increase of 2151 ppm by weight of propylbenzene (PB) and 562 ppm by weight of butylbenzene (BB) relative to base case Feed-B1. After a further 16 hours (Column "Effluent-D2S1") the PEB conversion was again measured and had increased to 66.7%.

After 167 hours on stream, a mixture of propylbenzene and butylbenzene was added to the feed to achieve an increase of 3975 ppm by weight of propylbenzene (PB) and 1015 ppm by weight of butylbenzene (BB) relative to base case Feed-B1. After a further 16 hours (Column "Effluent-D3S1") the PEB conversion was again measured and had increased to 68.6%.

After 211 hours on stream, a mixture of propylbenzene and butylbenzene was added to the feed to achieve an increase of 6049 ppm by weight of propylbenzene (PB) and 1544 ppm by weight of butylbenzene (BB) relative to base case Feed-B1. After a further 25 hours (Column "Effluent-D4S1") the PEB conversion was again measured and had increased to 69%.

After 259 hours on stream, a mixture of propylbenzene and butylbenzene was added to the feed to achieve an increase of 11957 ppm by weight of propylbenzene (PB) and 3042 ppm by weight of butylbenzene (BB) relative to base case Feed-B1. After a further 24 hours (Column "Effluent-D5S1") the PEB conversion was again measured and was 68.7%.

TABLE 1

|  |  | Feed-B1 | Effluent-B1S1 | Effluent-B1S2 | Effluent-B1S3 | Feed-D1 | Effluent-D1S1 | Effluent-D1S2 | Feed-D2 | Effluent-D2S1 | Effluent-D2S2 |
|---|---|---|---|---|---|---|---|---|---|---|---|
| Relative Time (in hrs) to Start of Experiment | | 0 | 18 | 39 | 63 | 69 | 88 | 118 | 118 | 134 | 159 |
| Outlet Pressure | psig | 400 | 403 | 402 | 400 | 400 | 400 | 400 | 400 | 402 | 400 |
| Fd Benzene/PEB | Ratio | 2.01 | 2.01 | 2.01 | 2.01 | 2.01 | 2.01 | 2.01 | 1.99 | 2.01 | 2.01 |
| WHSV | 1/h | | 3.3 | 3.3 | 3.3 | | 3.3 | 3.3 | | 3.3 | 3.3 |
| Avg. Temp. °C. | | | 205.9 | 205.9 | 205.7 | | 205.9 | 205.7 | | 205.8 | 206.0 |
| PEB Conv. | % | | 59.4% | 59.3% | 59.4% | | 63.7% | 63.5% | | 66.7% | 66.5% |
| PB in Total Stream | ppmw | 380 | 383 | 379 | 379 | 1,286 | 1,109 | 1,112 | 2,532 | 2,054 | 2,061 |
| BB in Total Stream | ppmw | 2,658 | 2,609 | 2,596 | 2,592 | 2,891 | 2,589 | 2,592 | 3,220 | 2,576 | 2,575 |
| ΔPB doped relative to Feed-B1 | ppmw | 0 | | | | 905 | | | 2,151 | | |
| ΔBB doped relative to Feed-B1 | ppmw | 0 | | | | 232 | | | 562 | | |

|  |  | Feed-D3 | Effluent-D3S1 | Effluent-D3S2 | Effluent-D3S3 | Feed-D4 | Effluent-D4S1 | Effluent-D4S2 | Feed-D5 | Effluent-D5S1 | Effluent-D5S2 |
|---|---|---|---|---|---|---|---|---|---|---|---|
| Relative Time (in hrs) to Start of Experiment | | 167 | 183 | 191 | 207 | 211 | 236 | 256 | 259 | 283 | 302 |
| Outlet Pressure | psig | 400 | 400 | 400 | 402 | 400 | 401 | 405 | 400 | 405 | 408 |
| Fd Benzene/PEB | Ratio | 1.99 | 1.99 | 1.99 | 1.99 | 2.00 | 2.00 | 2.00 | 2.00 | 2.00 | 2.00 |
| WHSV | 1/h | | 3.3 | 3.3 | 3.3 | | 3.3 | 3.3 | | 3.3 | 3.3 |
| Avg. Temp. °C. | | | 205.9 | 205.9 | 205.7 | | 206.0 | 206.0 | | 205.8 | 205.8 |
| PEB Conv. | % | | 68.6% | 68.3% | 68.1% | | 69.0% | 68.3% | | 68.7% | 67.8% |
| PB in Total Stream | ppmw | 4,356 | 3,463 | 3,469 | 3,470 | 6,430 | 5,062 | 5,108 | 12,338 | 9,609 | 9,601 |
| BB in Total Stream | ppmw | 3,673 | 2,596 | 2,605 | 2,590 | 4,202 | 2,584 | 2,617 | 5,700 | 2,582 | 2,571 |
| ΔPB doped relative to Feed-B1 | ppmw | 3,975 | | | | 6,049 | | | 11,957 | | |
| ΔBB doped relative to Feed-B1 | ppmw | 1,015 | | | | 1,544 | | | 3,042 | | |

The invention claimed is:

1. A process for producing ethylbenzene, the process comprising:
   (a1) supplying benzene and an alkylating agent comprising at least 40 wt % ethylene to an alkylation reaction zone;
   (b1) adding at least one $C_{3+}$ olefin to the alkylation reaction zone in an amount of at least 200 ppm by weight of the ethylene supplied to the alkylation reaction zone;
   (c1) contacting the benzene, ethylene and $C_{3+}$ olefin with an alkylation catalyst in the alkylation reaction zone under alkylation conditions effective to alkylate at least part of the benzene and produce an alkylation effluent comprising ethylbenzene, polyethylated benzene and at least one mono-$C_{3+}$ alkyl benzene;
   (d1) separating the alkylation effluent into at least a first product fraction comprising ethylbenzene and a second fraction comprising polyethylated benzene and said at least one mono-$C_{3+}$ alkyl benzene; and
   (e1) contacting at least part of the second fraction with benzene in a presence of a transalkylation catalyst under transalkylation conditions effective to convert at least part of the polyethylated benzene to ethylbenzene and produce a transalkylation effluent, wherein the second fraction comprises from 1000 to 18000 ppm by weight of propylbenzene and/or butylbenzene, and wherein the at least one $C_{3+}$ olefin is added separately to the alkylation reaction zone from the ethylene and benzene or is mixed with the alkylating agent and/or benzene prior to addition to the alkylation reaction zone.

2. The process according to claim 1, wherein the at least one $C_{3+}$ olefin is added to the alkylation reaction zone in an amount from 200 to 20,000 ppm of the ethylene supplied to the alkylation reaction zone.

3. The process according to claim 1, wherein the at least one $C_{3+}$ olefin comprises propylene and/or butene.

4. The process according to claim 1, wherein the alkylation catalyst comprises at least one zeolite selected from zeolite beta, a molecular sieve having a Constraint Index from 2 to 12 and a molecular sieve of the MCM-22 family.

5. The process according to claim 1, wherein the alkylation conditions include a temperature from 120° C. to 270° C., a pressure from 500 kPa to 8,300 kPa and a molar ratio of benzene to alkylating agent from 100:1 to 0.3:1.

6. The process according to claim 1, wherein the alkylation conditions are selected such that the benzene is at least partially in a liquid phase.

7. The process according to claim 1, wherein the second fraction comprises at least 20 wt % polyethylated benzene and at least 1000 ppm by weight of propylbenzene and/or butylbenzene.

8. The process according to claim 1, wherein the transalkylation catalyst comprises at least one zeolite selected from zeolite beta, zeolite Y, mordenite and a molecular sieve of the MCM-22 family.

9. The process according to claim 1, wherein the transalkylation conditions include a temperature from 100° C. to 300° C., a pressure of 8,000 kPa or less, a WHSV from 0.5 to 100 $hr^{-1}$ and a mole ratio of benzene to polyethylated benzene of from about 1:1 to about 30:1.

10. The process according to claim 1, wherein the transalkylation conditions are selected such that the second fraction is at least partially in a liquid phase.

11. The process according to claim 1, wherein the at least one $C_{3+}$ olefin is mixed with the alkylating agent prior to addition to the alkylation reaction zone.

12. The process according to claim 1, wherein the at least one $C_{3+}$ olefin is mixed with the benzene prior to addition to the alkylation reaction zone.

* * * * *